US012188387B2

(12) United States Patent
Cammack

(10) Patent No.: US 12,188,387 B2
(45) Date of Patent: Jan. 7, 2025

(54) OIL QUALITY MONITORING

(71) Applicant: Toyota Motor Engineering & Manufacturing North America, Inc., Plano, TX (US)

(72) Inventor: William Daryl Cammack, Frisco, TX (US)

(73) Assignee: Toyota Motor North America, Inc., Plano, TX (US)

( * ) Notice: Subject to any disclaimer, the term of this patent is extended or adjusted under 35 U.S.C. 154(b) by 74 days.

(21) Appl. No.: 16/704,605

(22) Filed: Dec. 5, 2019

(65) Prior Publication Data

US 2021/0172351 A1 Jun. 10, 2021

(51) Int. Cl.
| | |
|---|---|
| F01M 11/10 | (2006.01) |
| F01M 1/18 | (2006.01) |
| F16N 29/04 | (2006.01) |
| G01N 11/00 | (2006.01) |
| G01N 33/28 | (2006.01) |
| G07C 5/00 | (2006.01) |

(52) U.S. Cl.
CPC .............. *F01M 11/10* (2013.01); *F01M 1/18* (2013.01); *F16N 29/04* (2013.01); *G01N 11/00* (2013.01); *G01N 33/2888* (2013.01); *G07C 5/008* (2013.01); *F01M 2011/148* (2013.01)

(58) Field of Classification Search
CPC ...... F01M 11/10; F01M 1/18; F01M 2011/14; G01N 11/00; G01N 33/2888
USPC ....................................................... 701/29.5
See application file for complete search history.

(56) References Cited

U.S. PATENT DOCUMENTS

| | | | |
|---|---|---|---|
| 4,852,693 A | 8/1989 | Nakajima et al. | |
| 5,814,214 A | 9/1998 | Chun | |
| 6,301,531 B1 * | 10/2001 | Pierro | G07C 5/0841 |
| | | | 701/19 |
| 6,513,367 B2 | 2/2003 | Bondarowicz et al. | |
| 6,786,080 B2 | 9/2004 | Jakoby et al. | |
| 6,895,807 B2 | 5/2005 | Han et al. | |
| 7,498,932 B1 * | 3/2009 | Steffen | F01M 1/18 |
| | | | 123/196 R |
| 7,713,425 B2 | 5/2010 | Hanson et al. | |
| 7,921,703 B2 | 4/2011 | Keller et al. | |
| 8,127,597 B2 | 3/2012 | Staley et al. | |
| 9,623,350 B2 | 4/2017 | Rohrbach et al. | |
| 2003/0055666 A1 * | 3/2003 | Roddy | G07C 5/008 |
| | | | 705/305 |
| 2003/0083825 A1 * | 5/2003 | Berndorfer | F01M 11/10 |
| | | | 702/23 |
| 2003/0226809 A1 | 12/2003 | Zagone et al. | |
| 2004/0093150 A1 * | 5/2004 | Arai | F01M 11/10 |
| | | | 701/104 |
| 2004/0093291 A1 * | 5/2004 | Bodin | B60R 25/33 |
| | | | 705/35 |
| 2008/0302709 A1 | 12/2008 | Jefferies | |

(Continued)

*Primary Examiner* — Logan M Kraft
*Assistant Examiner* — Joshua Campbell
(74) *Attorney, Agent, or Firm* — Oblon, McClelland, Maier & Neustadt, L.L.P.

(57) ABSTRACT

To monitor oil quality of an automotive vehicle, a sensor generates a signal indicative of a characteristic of the oil. A processor is configured to determine the oil quality from the signal. A communication component transmits an indication of whether the determined oil quality meets an unacceptability criterion to an external device.

18 Claims, 4 Drawing Sheets

(56) References Cited

U.S. PATENT DOCUMENTS

| | | | |
|---|---|---|---|
| 2013/0268182 A1* | 10/2013 | Treharne | F02N 11/0829 903/905 |
| 2014/0019068 A1* | 1/2014 | Schneider | G01N 33/2888 702/30 |
| 2014/0365144 A1* | 12/2014 | Dvorak | G01N 33/2888 702/50 |
| 2015/0338386 A1* | 11/2015 | Chapman, III | F01M 11/10 702/50 |
| 2018/0031505 A1 | 2/2018 | Diez Garcia et al. | |

* cited by examiner

OIL QUALITY MONITORING

BACKGROUND

Modern automotive vehicles often require substantial financial outlays and may represent a large part of a household or company budget. Regular maintenance is a key practice for extending the life of an automotive vehicle, as is prompt attention to indicators of vehicle malfunction or diminished vehicle performance. One essential maintenance practice is to regularly change motor oil, as its quality diminishes with use at high engine temperatures. Typically, the oil changing interval is a function of mileage (e.g., 3,000 miles) or time in service (e.g., three months) rather than a function of the oil quality itself.

U.S. Pat. No. 8,127,597 describes an oil condition sensing device that determines an oil viscosity level and an oil change event. An engine control module includes an oil diagnosis module and an oil reporting module, where the oil reporting module provides visual or auditory, indicators of oil status to the driver, and estimates the amount of time to the next oil change. The estimation may be adjusted based on the oil viscosity. The oil reporting module determines oil change events based on the data from the oil diagnosis module.

While improvements in localized data processing of such sensor data are currently sought and are addressed in the present disclosure, skilled artisans will agree that research and development efforts are also being directed to expanding the applicability of such sensor data.

SUMMARY

To monitor oil quality of an automotive vehicle, a sensor generates a signal indicative of a characteristic of the oil. A processor is configured to determine the oil quality from the signal. A communication component transmits an indication of whether the determined oil quality meets an unacceptability criterion to an external device.

DETAILED DESCRIPTION

Figure 1:
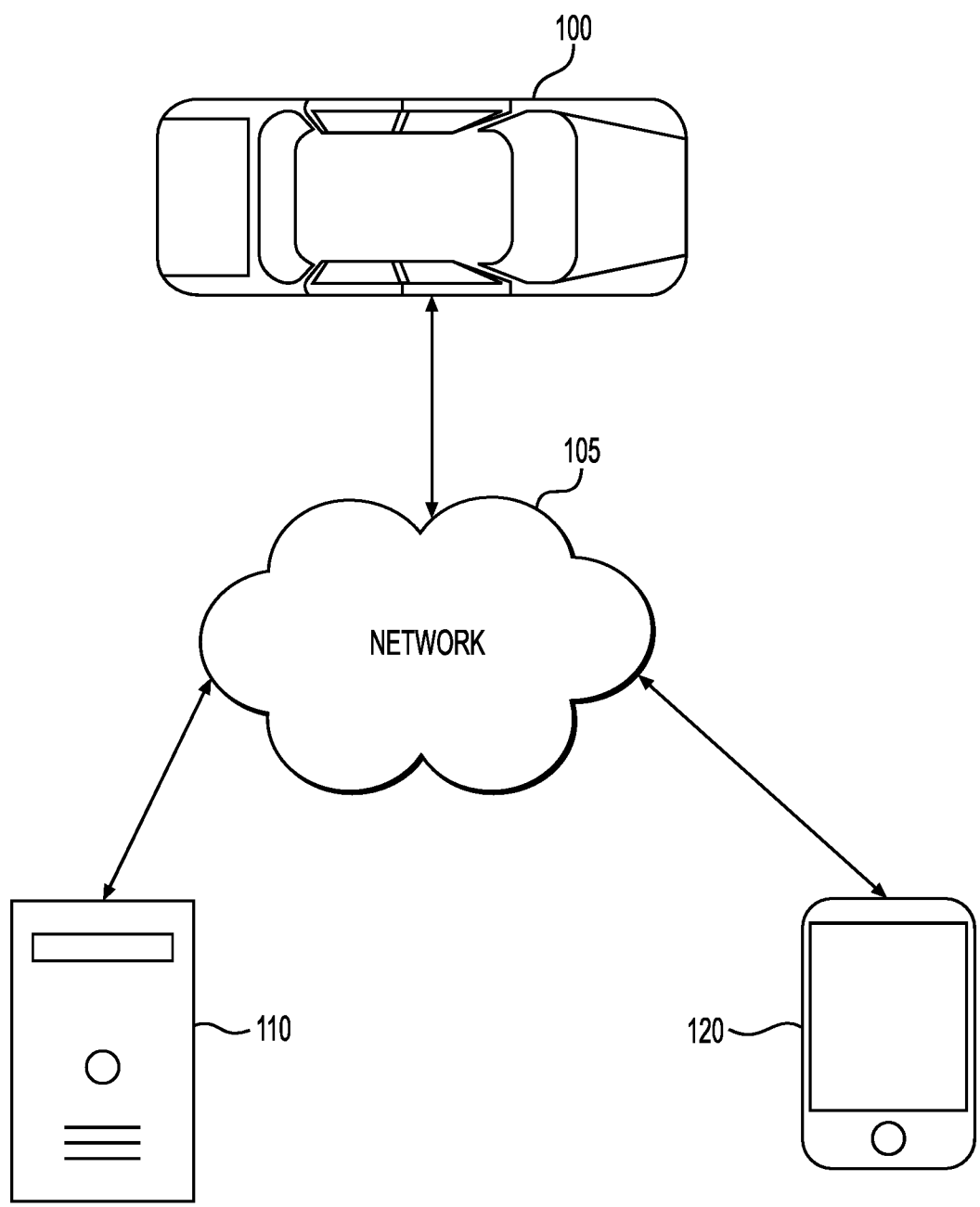
FIG. 1 is diagram of an example environment in which the present inventive concept can be embodied.

The present inventive concept is best described through certain embodiments thereof, which are described in detail herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, the word exemplary is used herein to mean, "serving as an example, instance or illustration." Any embodiment of construction, process, design, technique, etc., designated herein as exemplary is not necessarily to be construed as preferred or advantageous over other such embodiments. Particular quality or fitness of the examples indicated herein as exemplary is neither intended nor should be inferred.

FIG. 1 is diagram of an example environment in which the present invention can be embodied. As is illustrated, an automotive vehicle (or, simply vehicle 100) may be communicatively coupled to one or more server devices 110 (or, simply server 110) and/or one or more communication devices 120 through a communications network 105. As can be appreciated, communications network 105 can be a public network, such as the Internet, or a private network such as a LAN or WAN network, or any combination thereof and can also include PSTN or ISDN sub-networks. Network 105 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

Server 110 is implemented on hardware and software resources of an entity to interoperate with vehicle 100 and communication device 120 over network 105. The entity, such as a car dealership or an automobile manufacturer, may collect and analyze data from not only vehicle 100, but from a large number of other selected vehicles as well. In addition to data collection and analysis functionality, server 110 may further implement an outwardly facing interface or portal through which external devices, such as communication device 120, may access services and data provided by the entity. These and other features of server 110 are discussed below.

Communication device 120 is implemented on hardware and software resources of an entity to interoperate with vehicle 100 and server 110 over network 105. Communication device 120 may be operated by a vehicle owner or operator to interact with vehicle systems, such as those described below. Communication device 120 may be implemented through various technologies, such as cellular phones, smartphones, tablet computers, laptop computers, desktop computers and the like.

Figure 2:
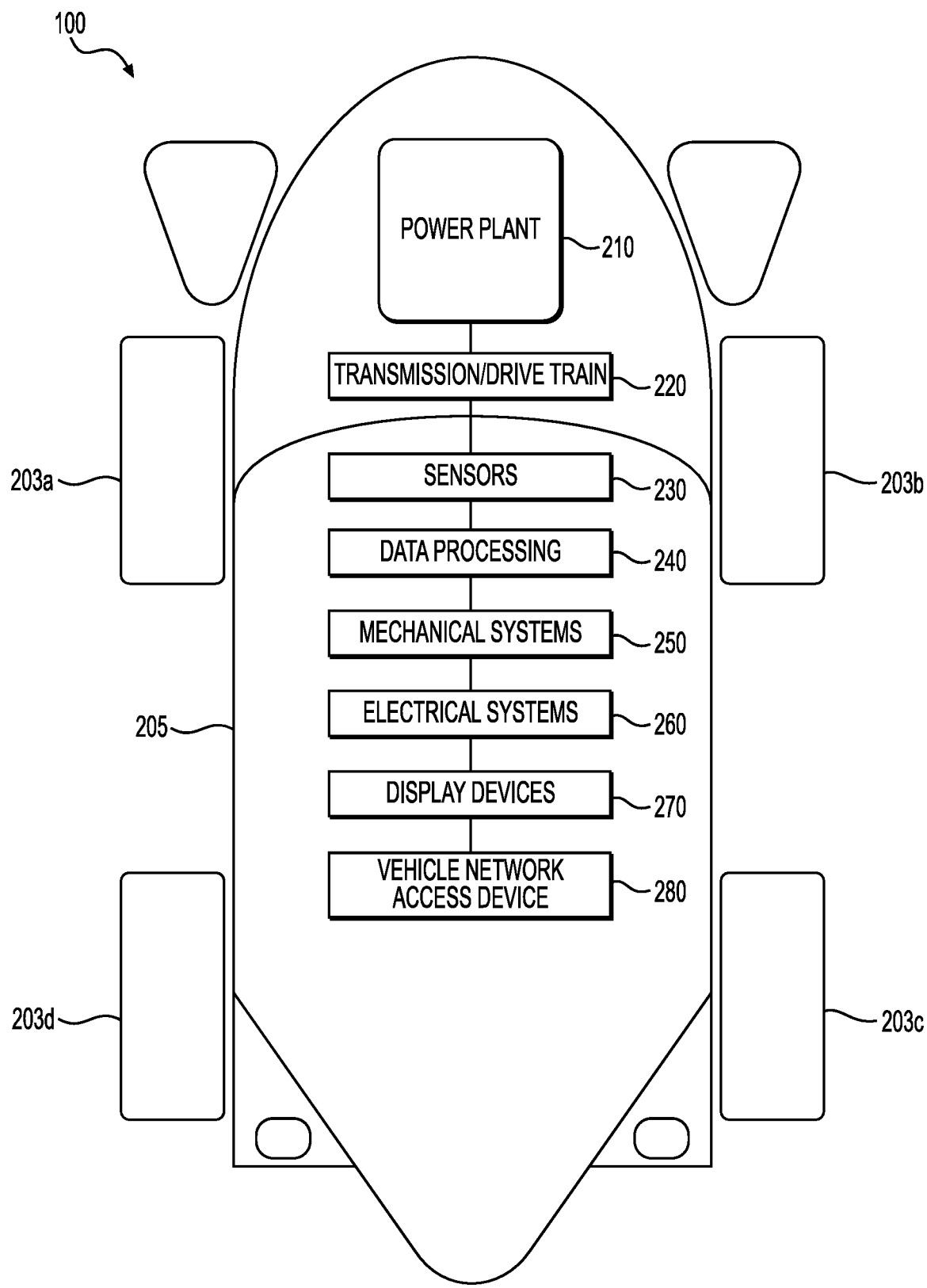
FIG. 2 is a schematic block diagram of an example vehicle embodying the present inventive concept.

FIG. 2 is a schematic block diagram of an example vehicle 100 embodying the present invention. FIG. 2 presents a set of vehicle systems in block form, where individual blocks in the figure represent physical manifestations of vehicular systems that include mechanisms described in more detail below. The systems represented in FIG. 2 are one set that can realize a fully functional automotive vehicle. Skilled artisans will recognize the physical manifestations of the systems associated with each block of FIG. 2 without explicit details being set forth herein.

Although the embodiment of FIG. 2 is illustrated and described as a road vehicle, upon review of this disclosure the skilled artisan will recognize how the principles of this disclosure can be applied in vehicles of other propulsion modes, e.g., aircraft, watercraft, hovercraft, etc. When vehicle 100 is embodied as a road vehicle, propulsion is achieved through a frictional engagement between wheels 203a-203d, representatively referred to herein as wheel(s) 203, and a road surface. Torque on wheels 203 may be provided by a power plant 210 that converts energy (internal combustion, electromotive) into rotational mechanical force. Wheels 203 are mechanically coupled to a vehicle body 205, in which a vehicle occupant would ride and/or cargo would be carried. Mechanical coupling between wheels 203 and vehicle body 205 may be implemented any number of ways, such as by use of a conventional vehicle chassis (not illustrated) and/or a conventional vehicle suspension system (not illustrated).

Vehicle 200 may be self-contained to the extent that it can carry a vehicle occupant (and/or cargo) along a trajectory, typically hundreds of miles long, without having to replenish its energy source (combustible fuel refill, battery recharge or both). Power plant 210 derives power from an energy source, such as gasoline and/or a battery, and applies a rotational force to wheels 203 through a transmission/drive train 220. These principles are well known and can be carried out by conventional means, except where otherwise indicated herein.

Distributed throughout vehicle 100 are numerous sensors 230; each generating a signal in response to a physical stimulus, e.g., pressure, temperature, position, voltage, current, velocity, torque, etc. Through such electrical signals, the state of vehicle 100 is obtained. As used herein, a vehicle state is defined by a selected (and often extensive) set of parameters associated with vehicular functionality. This includes base parameters such as the vehicle's speed, engine output, etc., but also includes parameters of other vehicle features, such as when the headlights are on and/or the turn signals activated. Vehicle state may include cabin temperature and entertainment system settings. Sensors 230 include the types and numbers of sensors necessary to determine the vehicle state at the granularity of information envisioned by a designer. To achieve various benefits of the invention, sensors 230 would include at least the techniques described in the example below.

Example data processing component 240 operates on, among other data, sensor data obtained from the aforementioned sensor signals to determine vehicle state information, which may be conveyed to a vehicle occupant through indicators or user interfaces implemented in vehicle 100. For example, when vehicle 100 is in an unsatisfactory state (e.g., oil quality measurement meets unacceptability criterion), embodiments of the invention may indicate such through an iconic dashboard indicator or dashboard message displayed on display devices 270, or any suitable way of providing the unsatisfactory state information to an end user, be that the driver or other occupant, a remote entity operating server 110 and/or operator of communication device 120. Additionally, the unsatisfactory vehicle state may compel action by a vehicle control unit, such as to limit vehicle operation based on unsatisfactory state information.

Vehicle 100 may include mechanical systems 250 that implement various mechanical functions of a fully functional automotive vehicle. Mechanical systems 250 may include conventional controls such as steering, accelerating, and braking, as well as other mechanically-operated user controls. Mechanical systems 250 may include environmental and safety mechanisms. The present invention can be embodied in a vehicle, such as vehicle 100, having any number of conventional mechanical systems in mechanical systems 250 that realize a fully functional automotive vehicle.

Vehicle 100 may include electrical systems 260 that implement various electrical/electronic functions. Electrical systems 260 comprise multiple electrical/electronic components, e.g., lamps, motors, solenoids, switches, electrical control circuits, entertainment systems, etc. typically interconnected by one or more wiring harnesses. Additionally, modern vehicles make use of processor circuits to implement monitor and control mechanisms. Thus, in certain embodiments, electrical systems 260 may include processing circuitry that implements control of vehicle 100. Electrical systems 260 include those electrical/electronic components necessary to realize a fully functional automotive vehicle. Those having skill in the art will recognize many different electrical/electronic components and circuits that can be implemented in various embodiments without departing from the principles described in this disclosure.

Display devices 270 may implement user interfaces that convey varied information to a vehicle operator and, in certain embodiments, afford vehicle control, such as through a touchscreen. Display devices 270 may be distributed throughout vehicle 100, such as on the dashboard or driver console and on the backs of cockpit seats for use by rear-seat occupants. Vehicle 100 may include display devices of different types, including individual lamps or indicators and high resolution LED display devices known in the art. The types and numbers of the display devices in display devices 270 will vary by vehicle design.

In certain implementations, vehicle 100 may include a vehicle network access device 280 by which vehicle 100 communicates with and is accessed by external devices, such as communication device 120 and server 110 illustrated in FIG. 1. Vehicle network access device 280 may include suitable communication circuitry to convey raw and processed information to external devices for purposes of maintenance, diagnostics, recordkeeping, and so on. A detailed example of such arrangement is provided below.

Figure 3:
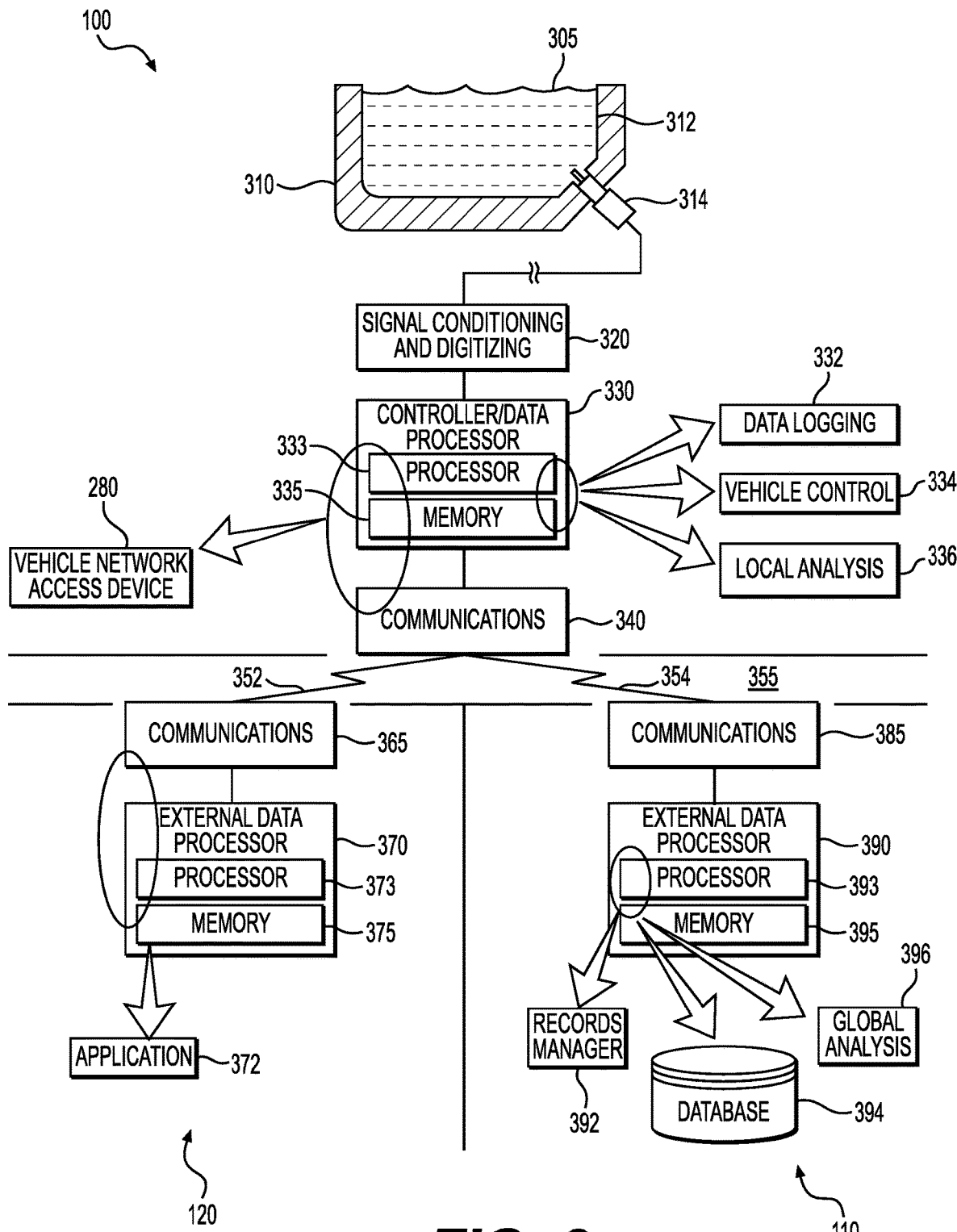
FIG. 3 is a schematic block diagram of an example system configuration by which the present inventive concept can be embodied.

FIG. 3 is a schematic block diagram of an example system configuration by which the present invention can be embodied. The principle components of the system described in FIG. 1, i.e., vehicle 100, communications device 120 and server 110, are illustrated at a different level of abstraction in FIG. 3. In FIG. 3, vehicle 100 is communicatively coupled with a communication device 120 and a server device 110 through communications links 352 and 354, respectively. Communications links 352 and 354 may be constructed in one or more media 355, such as would be underlying communications network 105 illustrated in FIG. 1. To that end, each of vehicle 100, communications device 120 and server 110 comprises communications components 340, 365 and 385, respectively. Communications components 340, 365 and 385 comprise circuitry suitable for constructing links 352 and 354 according to corresponding communication procedures and protocols. Those having skill in the communications arts will recognize numerous techniques by which such communications may be achieved without departing from the principles described in this disclosure.

Additionally, each of vehicle 100, communication device 120 and server 110 comprises computer resources at controller/data processor 330, external data processor 370 and external data processor 390, respectively. Each of these processor components comprise processor and memory resources: controller/data processor 330 comprises one or more processors 333 and memory 335; external data processor 370 comprises one or more processors 373 and memory 375; and external data processor 390 comprises one or more processors 393 and memory 395. Each of the processors may be implemented on microprocessors, microcontrollers, digital signal processors, field programmable gate arrays, application specific integrated circuits, programmable logic devices, or using discrete logic circuits, as one of ordinary skill in the art would recognize. The memories may be implemented on random access memory circuits, read-only memory circuits, volatile memory circuits, persistent memory circuits, etc. including hard disk drives, optical drives, flash drives, memory integrated circuits and other forms known to skilled artisans.

As illustrated in FIG. 3, one or more sensors 314 may be mechanically engaged in an engine block 310 and communicatively coupled to a cavity 312 in which a quantity of engine oil 305 flows or is otherwise contained. Sensor 314 may be any device suitable for measurements that characterize oil quality. In one embodiment, sensor 314 is a commercially available viscosity sensor threaded into an appropriate port in engine block 310. Other sensors may be used to determine oil quality, such as oil temperature sensors.

The electrical signal from sensor 314 may be conditioned (filtered, amplified, etc.) and, in certain embodiments, digitized (sampled) by signal conditioning and digitizing component 320 into computer data that can be operated on by computer resources of vehicle 100. These data will be referred to herein as raw sensor data and may be used to calculate oil quality using appropriate conversion, typically achieved through calibration data provided by the sensor manufacturer. The conversion may be achieved through a formula implemented by processor instructions stored in memory 335 and executed by processor 333. Alternatively, the conversion may be achieved through a suitable lookup table stored in memory 335.

As illustrated in FIG. 3, computer resources of vehicle 100 may realize a data logging component 332, by which oil quality data are timestamped and stored in data records in onboard memory 335. In certain implementations, these logged data records are transmitted to one or more external entities, such as communication device 120 and/or server 110. A vehicle identifier may be stored in memory 335 that can be transmitted with the logged data records so as to uniquely identify the dataset at the receiving entity. However, other implementations may omit transmitting all of the logged data records and may instead transmit indications of unfavorable conditions such as diminished oil quality.

Computer resources of vehicle 100 may implement a vehicle control component 334 by which vehicle systems are centrally controlled. Such control includes systems monitoring with responsive engine control, environmental (emissions) control, suspension control, cabin climate control and other automotive control functions known to skilled artisans. Additionally, vehicle control component 334 may be responsive to oil quality. For example, vehicle control component 334 may compel an indication that the oil quality meets a predetermined unacceptability criterion when such is the case. In certain embodiments, vehicle control component 334 may prevent engine operation if it is found that the oil quality meets the oil quality unacceptability criterion. It is to be understood that distributed control can also be implemented in embodiments, whereby different vehicle systems have a separate control component.

Computer resources of vehicle 100 may further implement a local analysis component 336. Local analysis component 336 may analyze data derived from various sensors of vehicle 100 to determine the state of vehicle 100. The state of vehicle 100 may be provided to vehicle control component 334 and a corresponding action or response may be compelled thereby. For example, the state of the vehicle may include an oil quality measurement and/or an indication that the oil quality meets an unacceptability criterion. The determination of whether the oil quality meets an unacceptability criterion may be a function realized by processor instructions stored in memory 335 and executed by processor 333. As one example, an oil quality measurement, e.g., oil viscosity, may be compared to a threshold value at which the oil is considered unacceptable (or approaching unacceptable) as a lubricant. Such threshold value may be established by the power plant designer and/or may be determined through chemical and mechanical analysis at the oil provider. Regardless of its origin, the threshold value may be stored in memory 335 and used in a comparison routine executed by processor 333.

Vehicle network access device 280 may be implemented on computer resources of controller/data processor component 330 and communication resources of communications component 340. When so configured, embodiments of the present invention can participate in a cloud computing environment and other coordinated communications via communication links 352 and 354. In one embodiment, the state of vehicle 100 includes an indication that the oil quality meets an unacceptability criterion. When such is the case, the state of the vehicle may be conveyed to communications device 120 and server 110.

Application 372 may be realized on computer and communication resources of communication device 110 and may allow monitoring and control of vehicle 100 via communications link 352. In certain implementations, various features of vehicle 100 are remotely controllable through application 372. Such control can remotely operate features such as remote start, lighting, etc., and may receive vehicle state information. Application 372 may send messages to and receive messages from vehicle control component 334 through vehicle network access device 337 through, for example, a user interface portion of application 372. Application 372 may comprise processor instructions stored in memory 375 and executed by processor 373 to communicate using communications component 365 with vehicle 100 and/or server 110.

Server 110 may include persistent storage on which a database 394 is constructed. In one embodiment, application 372 may access database 394 in a limited way through records manager 392, such as to maintain or otherwise view records on one's own vehicle. For example, application 372 may allow a user to enter oil maintenance information, such as date of oil change, type of oil, type of filter, etc., into the online records of the user's vehicle. Such information may alternatively be provided by an oil maintenance technician having a suitably configured application 372 at his/her disposal. These data may be maintained in the vehicle state information stored in memory 335 and may be used as input parameters of a mathematical model that predicts, among other things, the time the next oil change should be performed.

Database 394 may be constructed or otherwise configured to store massive amounts of data and may comply with various big data paradigms (e.g., data warehousing) known in the art. From the records of numerous vehicles of interest to an entity (manufacturer, automotive dealer, fleet manager, etc.), the aforementioned mathematical model may be constructed to provide a predicted output state for a given input state based on training on selected events recorded in database 394. Database 394 may thus contain training data as well as test data.

Computer resources of server 110 may further implement a global analysis component 396 that analyzes data in database 394 to discover new information from vehicle state information of many vehicles. In one implementation, global analysis component 396 may assess whether overall life expectancy of a particular motor oil in a particular engine, as measured over many similarly equipped vehicles' oil quality measurements, meets design specifications. Additionally, global analysis component 396 may implement more complex tasks, such as machine learning and predictive modeling to, for example, recommend oil maintenance procedures for particular vehicles given a particular oil quality measurement and other input parameters. To that end, global analysis component 396 may construct a mathematical model of power plant 210 that is trained on selected case data of database 394. Once trained, such a model may, for example, generate a vehicle state with a certain output parameter (e.g., time to next oil change) for a given vehicle state with certain input parameter(s) (e.g., current oil viscosity, oil temperature, time since last oil change).

Once a model has been constructed by global analysis component 396, it may be conveyed to local analysis component 336 via communication link 354, where the model may be applied to local oil quality events (e.g., oil quality meets or is approaching an unacceptability criterion). The output of the model may be a predicted state that includes a predicted time to next oil change based on a current state that includes local oil quality measurements. An indication of this predicted state may be provided to the relevant entities, e.g., vehicle occupant in vehicle 100, user of communication device 120 and entity in control of server 110.

In one example embodiment of the invention, power plant 210 is an internal combustion engine. Sensor 314 may be a viscosity sensor situated to maintain continuous contact with oil 305 in engine block 310. The electrical signal generated by sensor 314 may be sampled, such as by signal conditioning and digitizing component 320, into raw sensor data. These raw sensor data may be provided to local analysis component 336, whereby the raw sensor data are converted to viscosity values. In certain embodiments, the viscosity values may be logged by data logging component 332 and stored in data records of memory 335. Local analysis component 336 may receive a time-series of viscosity values (along with other values making up the state of vehicle 100) and determines whether an unacceptable viscosity event occurs. As used herein, an unacceptable viscosity event occurs when oil is no longer suitable as a lubricant. In response to an unacceptable viscosity event, e.g., the measured oil viscosity being greater than a predetermined unacceptable viscosity value, vehicle 100 may transition into an unacceptable viscosity state. In this state, vehicle control component 334 may compel lighting an indicator and/or displaying a message on display devices 270. Vehicle control component 334 may further transmit an indication of the occurrence of the unacceptable viscosity event to communication device 120 and/or to server 110.

In addition to vehicle-localized processing, vehicle network access device 280 may transmit the viscosity time series and/or the indication that the viscosity of engine oil 305 meets the unacceptability criterion to server 110. The data may be transmitted in association with a unique identifier, such as the vehicle identification number (VIN). The indication that the viscosity meets the unacceptability criterion may be added to records stored in database 394 via records manager component 392. As discussed above, maintenance records may be kept online in database 394, which may be accessed by application 372 of communication device 120.

Database 394 may contain the records of numerous vehicles, such as would be of interest to vehicle dealers and/or manufacturers. Analysis of such records may be performed by global analysis component 395, which may predict a time for next oil change through a suitable mathematical model. For example, global analysis component may identify that, for a certain engine design, the oil quality over a number of vehicles incorporating that engine design may depart from design specifications. Further analysis by vehicle designers may identify the cause of such shortcoming and corrective measures may be taken, including a vehicle recall. Other analyses may be performed by global analysis component as well.

In certain embodiments, vehicle network access device 280 may transmit the indication that the oil viscosity meets the unacceptability criterion to communication device 120. Such transmission may occur over the Internet and displayed on communication device 120 through application 372. Alternatively or additionally, the transmission may occur via a text message via cellular technology, should vehicle 100 be so equipped. Other notification techniques, such as email, may be used in embodiments as well.

Figure 4:
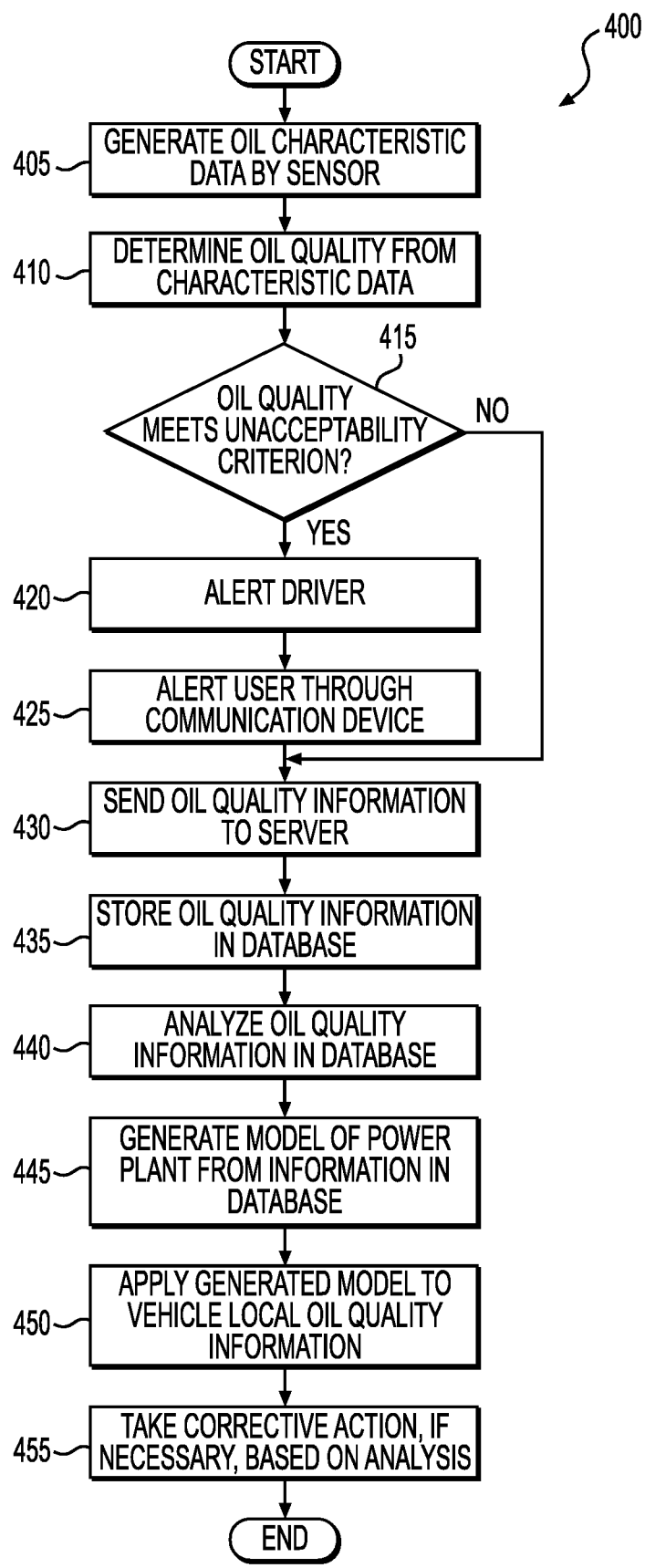
FIG. 4 is a flow diagram illustrating an example oil quality monitoring process by which the present inventive concept may be embodied.

FIG. 4 is a flow diagram illustrating an example oil quality monitoring process 400 by which the present inventive concept may be embodied. In operation 405, oil characteristic data may be generated by an oil quality sensor, such as an oil viscosity sensor or an oil temperature sensor. In operation 410, oil quality may be determined from the characteristic data and, in operation 415, it may be determined whether the determined oil quality meets an unacceptability criterion. If so, process 400 may transition to operation 420, whereby the driver (or other vehicle occupant) may be alerted to the low oil quality situation. In operation 425, a communication device user may be alerted as well. As illustrated in FIG. 4, operations 420 and 425 are omitted when the oil quality is acceptable. However, it is to be understood that oil quality, as a parameter, may be accessed through a communication device, such as through a portal application that allows access and display of various parameters of the vehicle.

In operation 430, oil quality information may be sent to a server and, in operation 435, the oil quality information may be stored in a database. In operation 440, the oil quality information stored in the database may be analyzed and used in operation 445 to generate a suitable model by which a predicted vehicle state is generated from a current vehicle state. In operation 450, the model is applied to local vehicle state data to determine the predicted state. In operation 455, corrective action may be taken, if necessary, based on the predicted state.

As will be appreciated by one skilled in the art, aspects of the present disclosure may be embodied as a system, method or computer program product. Accordingly, aspects of the disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present invention may take the form of a computer program product embodied in one or more computer readable medium(s) having computer readable program code embodied thereon.

Computer program code for carrying out operations for aspects of the disclosure may be written in any combination of one or more programming languages, e.g., an object oriented programming language such as Java, Smalltalk, C++ or the like, or a conventional procedural programming language, such as the "C" programming language or similar programming languages.

Aspects of the present disclosure are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, method and computer program products according to various embodiments of the disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending on the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the disclosure. The embodiment was chosen and described in order to best explain the principles of the inventive concept and the practical application, and to enable others of ordinary skill in the art to understand the inventive concept for various embodiments with various modifications as are suited to the particular use contemplated.

The descriptions above are intended to illustrate possible implementations of the present inventive concept and are not restrictive. Many variations, modifications and alternatives will become apparent to the skilled artisan upon review of this disclosure. For example, components equivalent to those shown and described may be substituted therefore, elements and methods individually described may be combined, and elements described as discrete may be distributed across many components. The scope of the invention should therefore be determined not with reference to the description above, but with reference to the appended claims, along with their full range of equivalents.

The invention claimed is:

1. An apparatus to monitor oil quality of an automotive vehicle, the apparatus comprising:
    a sensor that generates a signal indicative of a characteristic of oil;
    a processor configured to determine the oil quality from the signal; and
    a communication component to transmit over a communications network to a server external to the vehicle an indication of whether the determined oil quality meets an unacceptability criterion,
    wherein, when the determined oil quality meets the unacceptability criterion, the server is configured to:
        determine a model of oil degradation of the oil of the vehicle over time and over a number of miles traveled by the vehicle;
        compare the model of oil degradation of the vehicle to models of oil degradation of other vehicles that are of a same model as the vehicle and that have had their respective oil quality meet the unacceptability criterion, wherein the models of oil degradation of the other vehicles are based on time and number of miles traveled respectively by the other vehicles;
        determine based on the comparison whether the oil degradation of the vehicle occurs over a shorter distance or in less time than that of the other vehicles of the same model that have had their respective oil quality meet the unacceptability criterion; and
        when it is determined that the oil degradation of the vehicle occurs over a shorter distance or in less time than that of the other vehicles, instruct a controller of the vehicle to limit operation of the vehicle by preventing engine operation of the vehicle, and generate an analysis result including the determination of the oil degradation of the vehicle.

2. The apparatus of claim 1, wherein the indication of whether the determined oil quality meets the unacceptability criterion is transmitted to a mobile communication device over a cellular network as a text message.

3. The apparatus of claim 2, wherein the indication of whether the determined oil quality meets the unacceptability criterion is transmitted to the mobile communication device over a communications network as an email message.

4. The apparatus of claim 1 further comprising:
    a database implemented on the server and configured to store the oil quality information transmitted thereto.

5. The apparatus of claim 4, wherein the database contains maintenance records of the vehicle.

6. The apparatus of claim 1, wherein the sensor is a viscosity sensor.

7. The apparatus of claim 6, wherein the processor is further configured to:
   determine oil viscosity from the signal generated by the viscosity sensor;
   compare the oil viscosity with the unacceptability criterion; and
   compel an indicator to indicate that the oil quality meets the unacceptability criterion responsive to the comparing of the oil viscosity against the unacceptability criterion.

8. The apparatus of claim 1, wherein the processor is further configured to:
   predict a vehicle state that includes a predicted parameter from a current vehicle state that includes a current parameter of the oil quality.

9. The apparatus of claim 8, wherein the predicted parameter is time to next oil change.

10. The apparatus of claim 1, wherein the processor is further configured to:
    determine the oil quality from a signal generated by an oil quality sensor;
    compare the oil quality with the unacceptability criterion; and
    compel an indicator to indicate that the oil quality meets the unacceptability criterion responsive to the comparing of the oil quality against the unacceptability criterion.

11. An automotive vehicle comprising:
    a sensor that generates a signal indicative of a characteristic of oil;
    a processor configured to determine the oil quality from the signal; and
    a communication component to transmit over a communications network to a server external to the vehicle, an indication of whether the determined oil quality meets an unacceptability criterion,
    wherein, when the determined oil quality meets the unacceptability criterion, the server is configured to:
      determine a model of oil degradation of the oil of the vehicle over time and over a number of miles traveled by the vehicle;
      compare the model of oil degradation of the vehicle to models of oil degradation of other vehicles that are of a same model as the vehicle and that have had their respective oil quality meet the unacceptability criterion, wherein the models of oil degradation of the other vehicles are based on time and number of miles traveled respectively by the other vehicles;
      determine based on the comparison whether the oil degradation of the vehicle occurs over a shorter distance or in less time than that of the other vehicles of the same model that have had their respective oil quality meet the unacceptability criterion; and
      when it is determined that the oil degradation of the vehicle occurs over a shorter distance or in less time than that of the other vehicles, instruct a controller of the vehicle to limit operation of the vehicle by preventing engine operation of the vehicle, and generate an analysis result including the determination of the oil degradation of the vehicle.

12. The automotive vehicle of claim 11, wherein the indication of whether the determined oil quality meets the unacceptability criterion is transmitted to a mobile communication device.

13. The automotive vehicle of claim 11 further comprising:
    a database implemented on the server and configured to store the oil quality information transmitted thereto.

14. The automotive vehicle of claim 11, wherein the processor is further configured to:
    predict a vehicle state that includes a predicted parameter from a current vehicle state that includes a current parameter of the oil quality.

15. The automotive vehicle of claim 14, wherein the predicted parameter is time to next oil change.

16. A method of monitoring oil quality in an automotive vehicle, the method comprising:
    determining the oil quality from characteristic data generated by a sensor;
    determining whether the oil quality meets an unacceptability criterion; and
    transmitting over a communications network to a server external to the vehicle an indication that the oil quality meets the unacceptability criterion responsive to the oil quality meeting the unacceptability criterion,
    wherein, when the determined oil quality meets the unacceptability criterion, the server is configured to:
      determine a model of oil degradation of the oil of the vehicle over time and over a number of miles traveled by the vehicle;
      compare the model of oil degradation of the vehicle to models of oil degradation of other vehicles that are of a same model as the vehicle and that have had their respective oil quality meet the unacceptability criterion, wherein the models of oil degradation of the other vehicles are based on time and number of miles traveled respectively by the other vehicles;
      determine based on the comparison whether the oil degradation of the vehicle occurs over a shorter distance or in less time than that of the other vehicles of the same model that have had their respective oil quality meet the unacceptability criterion; and
      when it is determined that the oil degradation of the vehicle occurs over a shorter distance or in less time than that of the other vehicles, instruct a controller of the vehicle to limit operation of the vehicle by preventing engine operation of the vehicle, and generate an analysis result including the determination of the oil degradation of the vehicle.

17. The method of claim 16 further comprising:
    predicting a vehicle state that includes a predicted parameter from a current vehicle state that includes a current parameter of the oil quality.

18. The method of claim 17, wherein the predicted parameter is time to next oil change.

* * * * *